United States Patent

Terashi et al.

[11] Patent Number: 5,532,043
[45] Date of Patent: Jul. 2, 1996

[54] PHOTOREFLECTIVE SHEET

[75] Inventors: Mitugi Terashi, Matutou; Masaharu Inoue, Osaka; Yutaka Usijima, Takarazuka, all of Japan

[73] Assignee: Takase Dyeing & Printing Works, Ltd., Osaka, Japan

[21] Appl. No.: 358,986

[22] Filed: Dec. 19, 1994

Related U.S. Application Data

[63] Continuation of Ser. No. 118,196, Sep. 9, 1993, abandoned.

[30] Foreign Application Priority Data

Nov. 4, 1992 [JP] Japan ................... 4-337766
May 17, 1993 [JP] Japan ................... 5-114530

[51] Int. Cl.$^6$ .................. A01N 25/34; B32B 5/14; B32B 15/04
[52] U.S. Cl. .................. 428/152; 424/403; 424/408; 428/308.4; 428/318.4; 428/339; 428/402; 428/402.24; 428/423.1; 428/457; 428/905; 428/907; 428/912.2
[58] Field of Search ............... 47/2, 9; 424/400, 424/402, 403, 408; 428/224, 245, 246, 290, 332, 402.2, 402.24, 403, 404, 423.1, 457, 912.2, 907, 339, 402, 308.4, 318.4, 319.1, 905, 152, 141

[56] References Cited

U.S. PATENT DOCUMENTS 2,740,233  4/1954  Reynolds ................... 47/9
3,888,418  6/1975  Seith et al. ................ 239/145
4,326,359  4/1982  Tabacchi ................... 47/58
4,666,767  5/1987  Von Kohorn et al. .......... 428/304.4
4,794,726  1/1989  Fawcett et al. ............. 47/9
4,797,253  1/1989  Petersen ................... 428/196
4,981,689  1/1991  Shikinami et al. ........... 424/409
5,236,782  8/1993  Klug et al. ................ 428/402.21

Primary Examiner—Paul J. Thibodeau
Assistant Examiner—Stephen Sand
Attorney, Agent, or Firm—Fish & Richardson

[57] ABSTRACT

A photoreflective sheet comprising a resin foam sheet, a metal foil with an uneven shape in section laminated on a face of the sheet, and a base cloth laminated on the other face of the sheet is described. For agricultural use, laying the sheet under trees in orchards or hanging it from branches facilitates the growth and coloration of fruit even if the fruit are not well exposed to the sunshine, since the metal foil reflects sunshine in all directions. Further, a certain sustained-release preparation coating the back of the resin foam sheet protects fruit from certain pests such as animals, birds, insects, fungi and herbs. The middle resin foam sheet prevents a rise in temperature and dryness in soil. Also, the sheet can buffer the impact that the fruit dropped by a strong wind or heavy rain would receive. Consequently, the sheet provides an excellent effect so that damage to the fallen fruit is limited to the lowest level.

11 Claims, 5 Drawing Sheets

PHOTOREFLECTIVE SHEET

This application is a continuation of U.S. application Ser. No. 08/118,196, filed Sep. 9, 1993, now abandoned.

FIELD OF THE INVENTION

This invention relates to a photoreflective sheet for agricultural use in orchards, greenhouses and the like. The invention also relates to a photoreflective sheet comprising a chemical agent.

BACKGROUND OF THE INVENTION

Japanese Unexamined Utility Model Publication Nos. 81031 (1980) and 146147 (1986), and Japanese Examined Utility Model Publication No. 23150 (1982) proposed the use of photoreflective sheets to use sunlight more effectively for the growth of vegetables and fruits, and the coloration of fruits. Such a sheet was made of a base cloth covered with a metal foil (aluminum foil) for photo diffused reflection. The cloth was woven of a tape-type yarn like a slit yarn.

Other kinds of sheets using a photoreflective material such as a metal foil or a metal deposition film are known; for example, a reflective thermal sheet as proposed by Japanese Unexamined Utility Model Publication No. 174036 (1982). The reflective thermal sheet reported was made of a soft, synthetic resin film having a metal deposition layer on its face and a foam laminated on the film. Further, the use of a cushioned base material like an air mattress is proposed by Japanese Unexamined Utility Model Publication No. 103837 (1982).

Conventional photoreflective sheets were, however, less cushioned so that the sheets often damaged fruit, leaves, branches, etc. due to strong winds. Unexpectedly strong winds cause fruit to drop, resulting in a considerable deterioration of the commercial value of produce. A cushioned base like an air mattress made the sheet too expensive for large-scale agricultural use. In addition, such a cushion-type sheet was difficult to repair, lay out; or put away into storage. Conventional photoreflective sheets were merely intended to reflect sunlight onto fruits, and not to protect plants from pests such as animals, birds, insects, fungi, herbs or the like.

The invention provides a photoreflective sheet which is soft, light, appropriately cushioned and superior in photo diffused reflection.

The invention also provides a photoreflective sheet which reflects sunlight suitably to plants, and which contains a certain chemical preparation to protect the plants from pests.

SUMMARY OF THE INVENTION

To accomplish the above objectives, a first photoreflective sheet of the invention comprises a resin foam sheet, a metal foil laminated on a first face of the resin foam sheet and a base cloth laminated on a second face of the resin foam sheet. The sheet is characterized in that the metal foil is uneven in section.

A second photoreflective sheet of the invention comprises a resin foam sheet, a metal foil laminated on a first face of the resin foam sheet and a base cloth laminated on a second face of the resin foam sheet; the resin foam sheet further comprises a porous microcapsule containing at least one selected from the group consisting of an animal, bird or insect repellent, an insecticide, a herbicide and a fungicide, which are applied to a face of the base cloth.

In a preferred embodiment of the first and second photoreflective sheets, the uneven shape of the metal foil derives from shrinkage of the base cloth on the resin foam sheet to provide photo diffused reflection.

It is also preferable in an embodiment of the first and second photoreflective sheets that the metal foil and/or base cloth is laminated on the resin foam sheet by fusion-welding the resin foam sheet to provide adhesive strength.

It is also preferable in an embodiment of the first and second photoreflective sheets that the resin foam sheet comprises polyurethane, in order to provide flexibility.

It is also preferable in an embodiment of the first and second photoreflective sheets that the thickness of the resin foam sheet is about 1 to 5 mm. It is also preferable in an embodiment of the first and second photoreflective sheets that the base cloth is shrinkable, so that the base cloth effectively gives the metal foil the uneven shape.

It is also preferable in an embodiment of the second photoreflective sheet that the porous microcapsule is a condensation of an inorganic porous granule so that a sustained release preparation in the microcapsule can effectively work.

It is also preferable in an embodiment of the second photoreflective sheet that the porous microcapsule contains at least one selected from sustained release preparations consisting of an animal, bird or insect repellent, an insecticide, a herbicide and a fungicide to provide a durable effect of the chemical.

For agricultural use, laying the photoreflective sheet of the invention under trees in an orchard or hanging it from trees can facilitate the growth and coloration of fruits even if they are not well exposed to the sun, because a surface metal foil of the sheet diffuses sunlight in all directions. Furthermore, coating a certain chemical on the rear of the sheet protects the produce from animals, birds, insects, fungi, herbs, etc. When the sheet, hung from a tree or a branch, contacts branches, leaves, fruit, etc., the sheet will not damage them. In addition, if the sheet is laid on soil, its middle resin foam sheet can prevent too great a rise in temperature and dryness in soil; moreover, the middle resin foam sheet can buffer the impact that falling fruits would receive. Consequently, loss due to damaged fruit is limited to the lowest level.

DETAILED DESCRIPTION OF THE INVENTION

Figure 1:
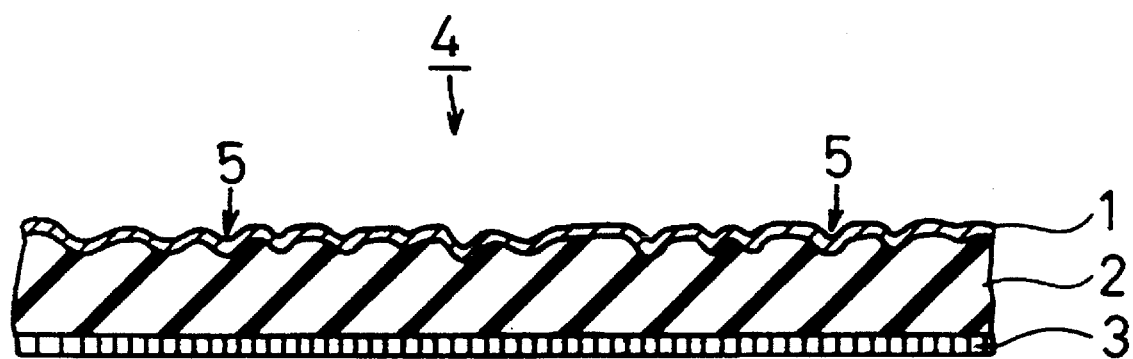
FIG. 1 is a cross-sectional view of a photoreflective sheet of a preferred embodiment of the invention.

A resin foam of the invention can be made of various resin foam sheets; for example, a polyurethane foam, a polyethylene foam, a polystyrene foam, a silicone rubber foam, a biodegradable cellulose foam and the like.

When using polyurethane, for example, the polyurethane foam sheet should be of a thickness of 1 to 10 mm, preferably 2 to 5 mm. A sheet less than 1 mm thick lacks sufficient elasticity. On the other hand, a sheet more than 10 mm thick is less economical, and has great difficulties in forming an indefinitely uneven shape of a metal foil. For the polyurethane foam, a relatively high expansion ratio, i.e., more than 7-fold increase, is preferable because the shrink of the base cloth will crease a photoreflective layer, as will be explained later. An open cell foam is preferable to a closed cell foam.

A preferable metal foil is of aluminum or stainless steel in a thickness of 10 to 20 μm having a total reflection rate of 80% or more, against a tungsten lamp.

A thermally-shrinkable base cloth can be a woven or knitted cloth, or a synthetic resin sheet, both of which shrink horizontally about 5 to 30% at a temperature below the melting point of the polyurethane foam sheet. Also, the base cloth can preferably be a cloth capable of shrinking at relatively low temperature, for example, a sheeting woven with a spun yarn of an acrylic or a polypropylene fiber, since such a sheeting is light, soft and less expensive. Furthermore, heating the surface of a polyurethane foam sheet makes the surface as cohesive as adhesives. Thus, a trilayer of the metal foil/polyurethane foam sheet/base cloth is effectively formed by quickly laminating the base cloth and the metal foil without adhesives. The rear of the base cloth is thermally shrunk. Thus, a metal foil on the base cloth makes a crease-like indefinitely uneven shape derived from the polyurethane foam sheet.

In detail, the crease-like indefinitely uneven shape is formed as follows: a face of polyurethane foam sheet is heated and fused by a gas burner, and immediately a thermally-shrinkable base cloth or a metal foil is tightly glued to the fused face. The other face of the polyurethane foam sheet is similarly heated and fused, and immediately a metal foil or a thermally-shrinkable base cloth is tightly glued to the fused face. Afterwards, to shrink the base cloth for an intended crease-like indefinitely uneven shape, the trilayer of the metal foil/polyurethane foam sheet/base cloth is subjected to heat treatment under no restriction. If necessary, porous microcapsules containing at least one selected from the group consisting of an animal, bird or insect repellent, an insecticide, a herbicide and a fungicide are applied to a face of the base cloth as follows.

First, porous microcapsules are formed by making a condensation of, for example, silica, calcium silicate, or alumina etc. with a particle size of about 5 μm mean outside diameter by the interface reaction method, and confining the selected chemical as a core of the condensation. Then, the inorganic porous microcapsules of 1.5 to 10 parts by weight are mixed with an acrylic resin (resin coating material) of 100 parts by weight to prepare an emulsion, which will be applied to coat the base cloth on the rear of the photoreflective sheet.

The following compositions are applicable for the invention;

(1) Extracts from ginkgo leaves: 6-alkenylsalicylic acids, sesquiterpenes such as ginkgolides and bilobalide.
(efficacy) repellency for the green caterpillar and army worm;

(2) Extracts from mugwort: mugwort oil.
(efficacy) repellency for the crow, brown-eared bulbul, rufous turtled dove, and gray starling;

(3) Extracts from bark, root bark, branches and leaves of camphor trees: cinnamic aldehyde and ortho cinnamic aldehyde.
(efficacy) repellency for thrips injurious to oranges and persimmons;

(4) Extracts from roses: rose perfumes, geraniol, benzylaldehyde, tetrahydrolinalool, and cyclamem aldehyde.
(efficacy) repellency for the pigeon, sparrow, crow, gray starling, and brown-eared bulbul;

(5) Extracts from *Chrysanthemum cinerariaefolium*: pyrethrin,
Extracts from derris: rotenone,
Extracts from tobacco: nicotine,
Extracts from *Pieris japonica*: Asebotoxins.
(efficacy) repellency for the mouse, rabbit, crow, sparrow, gray starling, brown-eared bulbul, grasshopper, leafhopper, and aphid;

(6) Extracts from Japanese cedar leaves, bamboo leaves, and aspidistras: extract of 55% purity containing an anti-oxidizer of vitamins $B_1$, $B_2$ and $B_6$ and a small amount of citric acid.
(efficacy) disinfection;

(7) Creosote and pyridine.
(efficacy) repellency for the crow, brown-eared bulbul, rufous turtled dove, and gray starling;

(8) Stimulative spices: powders or extract from a solvent such as an alcohol of pepper, cayenne pepper, mustard, Japanese horseradish (wasabi), garlic, onion, turmeric, cinnamon, allspice, and cardamom;
Fragrant spices: powders or extract from a solvent such as an alcohol of clove, thyme, peppermint, perilla, sage, and Japanese pepper (sanshou).
(efficacy) repellency for the dog, cat, and dove;

(9) Acetylphosphoramidethioic acid O,S-dimethyl ester.
(efficacy) repellency and control for aphids, thrips, the greenhouse whitefly, green caterpillar, diamond-back moth, army worms, lawn grass cutworm, and bluegrass webworm;

(10) An organic or inorganic compound containing a metal ion such as copper or silver.
(efficacy) disinfection.

(11) Herbicides, for example, chlorate herbicides such as sodium chlorate, halide fatty acid herbicides, carbamate herbicides, or their mixture.

The preferred embodiments of the invention will hereinafter be explained. It should be understood that the embodiments are not intended to limit the invention.

EXAMPLE 1

A. Formation of photoreflective sheet.

An example of the formation of a photoreflective sheet will be explained with reference to the accompanying drawings. FIG. 1 is a cross-sectional view of a photoreflective sheet (4) in which a reference numeral (1) designates a metal foil, (2) a polyurethane foam sheet, and (3) a thermally-shrinkable base cloth. The metal foil (1) was formed of a 13 μm thick aluminum foil. The polyurethane foam sheet (2) was formed of a 2 mm thick soft polyurethane foam sheet with a specific gravity of 0.020 capable of thermal fusing. The thermally-shrinkable base cloth (3) was formed of a highly shrinkable coarse plain-weave sheeting, which was woven using an acrylic spun yarn of No. $14^S$ count as a warp and a weft. The density of the warp and the weft was 17 threads/inch. The photoreflective sheet (4) comprised the polyurethane foam sheet (2), the metal foil (1) laminated thereon, and the thermally-shrinkable base cloth laminated on the rear of the polyurethane foam sheet (2). Thermal shrink in the base cloth (3) gave the metal foil (1) a crease-like indefinitely uneven shape (5) through the polyurethane foam sheet (2).

Figure 2:
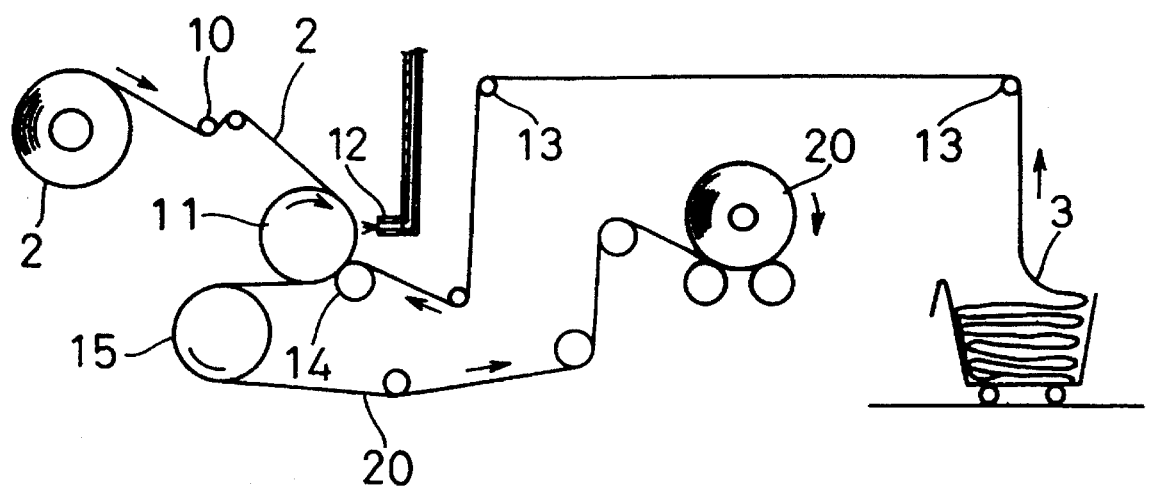
FIG. 2 is an illustration of a first step of a method of a preferred embodiment of the invention.

Next, a method of forming the photoreflective sheet (4) will be explained with reference to FIGS. 2, 3 and 4. Referring first to FIG. 2, a 1350 mm wide polyurethane foam sheet (2) was drawn out of a roll thereof. Tension enough not to loosen the polyurethane foam sheet (2) was applied to the sheet (2) with a swivel tension device (10). The sheet (2) was pulled to a main roller (11) rotating at a speed of 40 m/min. The 0.4 to 0.6 mm thick outer face of the sheet (2) was heated by a gas burner (12) to fuse with a thermally-shrinkable base cloth (3). On the other hand, through guide rollers (13) the base cloth (3) was introduced to a press roller (14) located under the gas burner (12). There, the base cloth (3) contacted a peripheral face of the main roller (11). The press roller (14) applied pressure to the base cloth (3) to fuse with the sheet (2). The fused base cloth (3) and sheet (2) was cooled by a cooling roller (15) to form a bilayer sheet (20), which was temporarily rolled. The base cloth (3) was not thermally shrunk during this operation.

Figure 3:
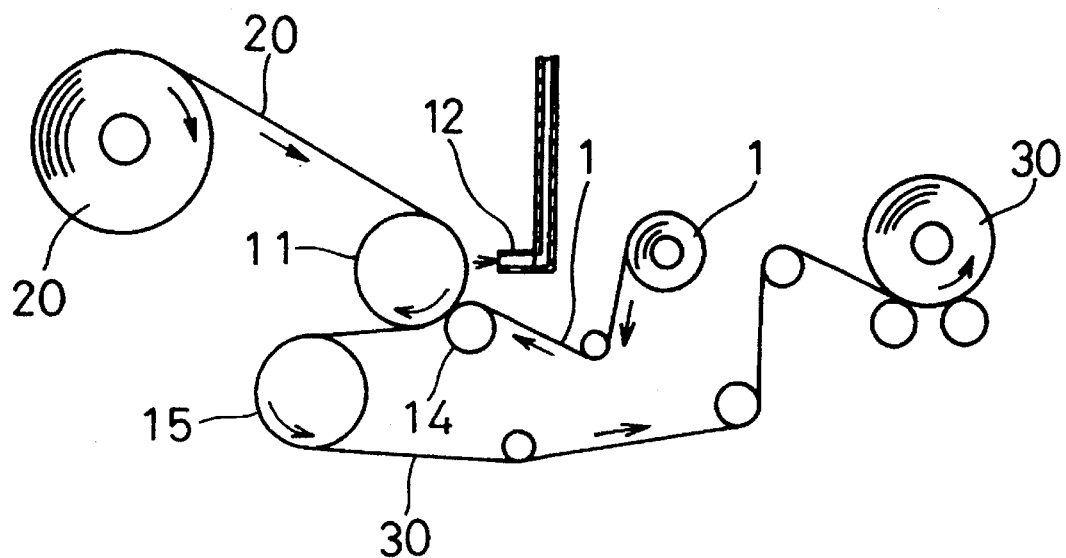
FIG. 3 is an illustration of a second step of a method of a preferred embodiment of the invention.

Next, as shown in FIG. 3, the bilayer sheet (20) composed of the polyurethane foam sheet (2) and the base cloth (3), both of which are not shown in FIG. 3, was supplied to a device comprising the main roller (11), the gas burner (12), the press roller (14), and the cooling roller (15), such that the face of the polyurethane foam sheet (2) was upside. Tension was applied to the bilayer sheet (20), but not enough to loosen it. The bilayer sheet (20) was similarly heated by the burner (12) to slightly fuse the surface of the polyurethane foam sheet (2). The metal foil (1) was contacted and fused to the polyurethane foam sheet (2). A trilayer sheet (30) of the polyurethane foam sheet (2), the metal foil (1) fused thereon and the base cloth (3) laminated on the other face of the sheet (2) was thus formed and cooled before being rolled into a cylindrical shape.

Figure 4:
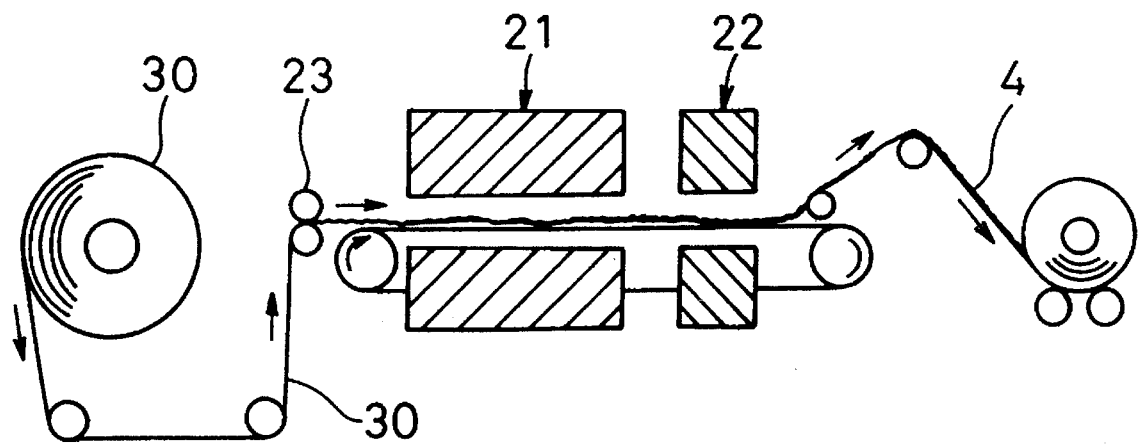
FIG. 4 is an illustration of a heat treatment of a preferred embodiment of the invention.

As shown in FIG. 4, the trilayer sheet (30) was then introduced to a heat treatment device provided with a heating cell (21) and a cooling cell (22) without restricting the shrink such that the face of the base cloth (3) (not shown in FIG. 4) was outside and the face of the metal foil (1) (not shown in FIG. 4) was inside. The trilayer sheet (30) was supplied into the heat treatment device after being loosened by a feeding roller (23). In the heating cell (21) the base cloth (3) in the trilayer sheet (30) was shrunk horizontally and vertically. The base cloth (3) was then cooled in the cooling cell (22) before being rolled into a cylindrical shape. After the heat treatment, the base cloth (3) was shrunk by 8% both horizontally and vertically. The base cloth (3) conveyed its shrinkage to both the polyurethane foam sheet (2) and the metal foil (1). As shown in FIG. 1, the metal foil (1) had an indefinitely uneven shape (5) with a height of about 1–2 mm even though the rear base cloth (3) was flat. The metal foil (1) was firmly bonded to even concavities of the polyurethane foam sheet (2). The trilayer sheet (30) kept the shape (5), and was very elastic in the side of the metal foil (1). The uneven shape (5) had no sharp flaw like that made by the embossment process. Therefore, the entire face of the metal foil (1) was photoreflective.

For reference, presented below are results of the washing method test for examining durability of the photoreflective sheet of the present embodiment, especially the uneven shape.

| | |
|---|---|
| (1) Washing test in accordance with JIS-L-027.103 | |
| 5 repetions | The 5th rate |
| (2) Commercial washing test (chloric dry-cleaning) | |
| Once | The 4th rate |
| (3) Commercial washing test (oily dry-cleaning) | |
| Once | The 4th rate |

This is a rating of a used sheet's appearance compared with new ones on five levels.

In the present embodiment, the trilayer sheet (30) was formed by two steps: (i) pasting the polyurethane foam sheet (2) to the base cloth (3), and (ii) pasting the metal foil (1) to the polyurethane foam sheet (2). It can also be formed in reverse order. Further, the bilayer sheet (20) can be moved forward without rolling it into a cylindrical shape. The metal foil (1) or the base cloth (3) can be laminated on such a running bilayer sheet (20).

B. Effects of photoreflection.

A 10×20 cm photoreflective sheet of the present embodiment was folded in two with its metal face outward, and was attached to branches of a mikan orange tree. The mikan trees used were 7 years old. On one tree, 30 photoreflective sheets were attached. Fully ripened mikan fruits were provided by the tree three weeks earlier than trees without photo reflective sheets.

Further, for agricultural use, placing the photoreflective sheet under trees in orchards with a face of its metal foil (1) outward can facilitate the growth and coloration of the fruit. This is because the sheet diffuses sunlight to the fruit in the same way as conventional sheets. Also, the sheet prevents dryness in soil and inhibits growth of weeds. If an unexpectedly strong wind or heavy rain drops some fruits from the trees, a cushioned sheet on soil can buffer the impact that the fruits would receive. Consequently, the sheet provides an excellent effect in that damage to the fallen fruits is limited to the lowest level.

EXAMPLE 2

A. Example of forming a photoreflective sheet.
A photoreflective sheet was formed in the same manner as in Example 1, A.

B. Example of micro-encapsulation of a repellent.
To form repellent microcapsules, a mixture of compositions was packed into microcapsules made by the silica intersurface reaction with an average outside diameter of 5 μm. The compositions used were:

cinnamic aldehyde and ortho cinnamic aldehyde (extracts from barks and leaves of camphor trees), 6-alkenylsalicylic acids and sesquiterpenes (extracts from ginkgo leaves), and extracts from Japanese cedar leaves, bamboo leaves and aspidistras. To the repellent microcapsules were kneaded 20 wt % of water and 0.1 wt % of a dispersing agent with a roller. An aqueous solution of a dispersed acrylic resin was added to the repellent microcapsules, which were kneaded again. The amount of the acrylic resin equaled a ten-fold weight of the microcapsules.

Figure 5:
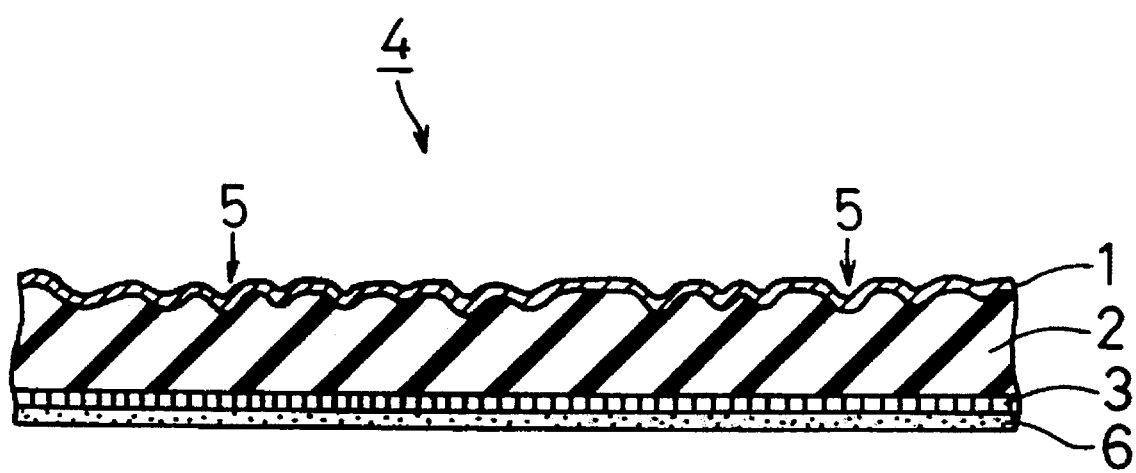
FIG. 5 is a cross-sectional view of a photoreflective sheet of a preferred embodiment of the invention which is coated with a chemical agent.

C. Example of repellent-microcapsule coating.
The above kneaded resin and repellent microcapsules were contacted using a roller with the rear of the photo diffuse reflective sheet explained above. The resin was dried with hot air at 60° C. To the sheet was adhered a resin in the repellent microcapsules of 10 g/m² after drying. FIG. 5 is a cross-sectional view of a preparation-coating photoreflective sheet in which the microcapsule layer (6) coats a face of the base cloth (3).

D. Repellency for animals, birds and insects.

Figure 6:
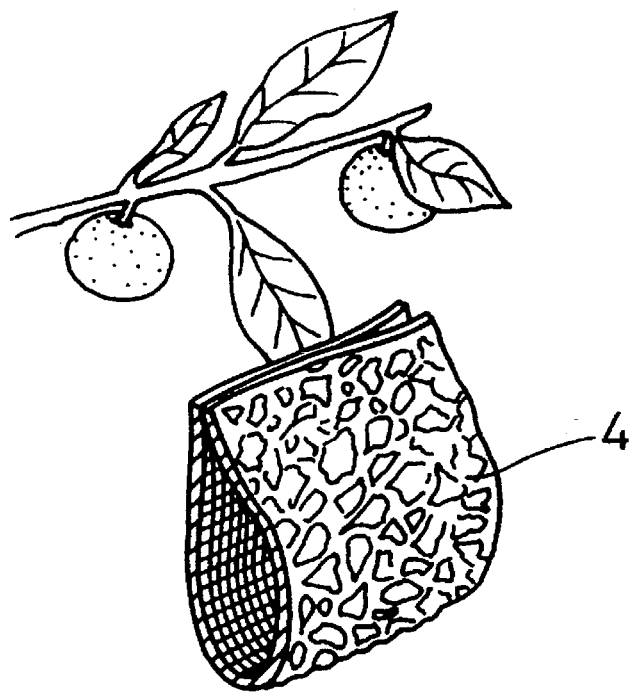
FIG. 6 is an explanatory illustration in which a photoreflective sheet coated with a chemical agent is hung on a leaf of a sweet summer orange.

(a) A 15×30 cm photo reflective sheet of the present embodiment was folded in two with its metal face outward. As FIG. 6 shows, the sheet was attached on a leaf of a sweet summer orange tree using a stapler. Four hundred trees in a 1-hectare area were used a month before harvest. On each tree, 10 sheets were evenly attached. For a month afterwards, all the trees were unaffected by pests. On the other hand, in a field next to the experimental area, other sweet summer orange trees having no photoreflective sheets had their fully ripened, attacked by flocks of brown-eared bulbul, gray starlings, and crows. As a result, about 30% of the yield was damaged.

Figure 7:
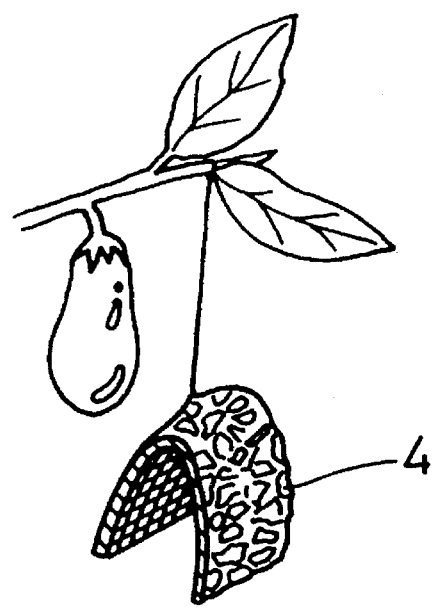
FIG. 7 is an explanatory illustration in which a photoreflective sheet coated with a chemical agent is hung on a stalk of an eggplant.

(b) As FIG. 7 shows, a photoreflective sheet was hung on an eggplant in a greenhouse using a thread. Five sheets were hung on one plant. No slugs, aphids and *Thrips palmi* Karny were attracted to the plants.

As explained above, the photoreflective sheet (4) of the present embodiments comprised the polyurethane foam sheet (2), the metal foil laminated thereon, and the thermally-shrinkable base cloth (3), which gave the metal foil (1) the crease-like indefinitely uneven shape (5). For example, for agricultural use, laying the photoreflective sheet under trees in orchards with a face of its metal foil (1) outward facilitates the growth and coloration of fruit because the sheet diffuses sunlight to the fruit.

Furthermore, the sheet prevents weeds and dryness in soil. If a strong wind or heavy rain like a typhoon drops fruit from the trees, the cushioned sheet buffers the impact that the fruit would receive. Consequently, the sheet provides an excellent effect in that damage to the fallen fruit is limited to the lowest level.

Furthermore, a core layer of the polyurethane foam sheet (2) and the base cloth (3) is soft and light enough to permit easy handling, and application on an inside wall of a greenhouse or to use in thermally packaging fruit.

According to the method of forming the photoreflective sheet, the metal foil (1), the polyurethane foam sheet (2) and the base cloth (3) are integrated into the trilayer sheet (30), making use of adhesion of the polyurethane foam sheet (2), and not adhesives. Thus, a cushioned sheet superior in photo reflection is effectively provided.

The middle polyurethane foam sheet (2) is composed of open cells. The sheet (2) having a number of tiny pores lets water go into soil and holds some of the rain, preventing dryness in soil. As sheet (2), alternatively, both a closed cell sheet and an open cell sheet can be used together to maintain warmth and reduce a sudden fluctuation in temperatures of soil, and can be used in a greenhouse for the growth of produce.

As explained above, a photoreflective sheet of the present invention comprises a resin foam sheet, a metal foil with an uneven shape in section laminated on a face of the sheet, and a base cloth laminated on the other face of the sheet. For agricultural use, for example, laying the sheet under trees in orchards or hanging it from branches facilitates the growth and coloration of fruit even if the fruit are not well exposed to sunshine, since the metal foil reflects sunlight in all directions. Further, a certain sustained-release preparation coating the rear of the resin foam sheet protects the fruit from certain pests such as animals, birds, insects, fungi and herbs. The middle resin foam sheet checks the rise of temperature and dryness in soil. Also, the sheet can buffer the impact that fruit would receive if a strong wind or heavy rain detaches the fruit from the trees. Consequently, the sheet provides an excellent effect so that damage to the fallen fruit is limited to the lowest level.

The invention may be embodied in other specific forms without departing from the spirit or essential characteristics thereof. The disclosed embodiments are to be considered in all respects as illustrative and not restrictive, the scope of the invention being indicated by the appended claims rather than by the foregoing description and all changes which come within the meaning and range of equivalency of the claims are intended to be embraced therein.

What is claimed is:

1. A photoreflective sheet comprising a resin foam sheet, a continuous metal foil laminated on a first face of said resin foam sheet wherein the metal foil covers all of the first face of the resin foam sheet, and a thermally-shrinkable base cloth laminated on a second face of said resin foam sheet, wherein said metal foil has an uneven surface with creases to provide photodiffused reflection and wherein the creases are formed by thermally-shrinking said thermally-shrinkable base cloth laminated on said resin foam sheet.

2. A photoreflective sheet according to claim 1, wherein one of the metal foil or the base cloth is laminated to the resin foam sheet by fusion-welding.

3. A photoreflective sheet according to claim 1, wherein both the metal foil and the base cloth are laminated on the resin foam sheet by fusion-welding.

4. A photoreflective sheet according to claim 1, wherein the resin foam sheet is a polyurethane foam sheet.

5. A photoreflective sheet according to claim 1 or 4, wherein the thickness of said resin foam sheet is from about 1 to 5 mm.

6. A photoreflective sheet comprising a resin foam sheet, a continuous metal foil laminated on a first face of said resin foam sheet, said metal foil having an uneven surface with creases to provide photodiffused reflection, wherein the metal foil covers all of the first face of the resin foam sheet, and a shrinkable base cloth laminated on a second face of said resin foam sheet, wherein the shrinkable base cloth further comprises a resin having microcapsules containing at least one agent selected from the group consisting of a repellent for animals, a repellent for birds, a repellent for insects, an insecticide, a herbicide, and a fungicide, wherein the creases are formed in the uneven surface of said metal foil by shrinkage of said base cloth.

7. A photoreflective sheet of claim 6, wherein said porous microcapsule comprises an inorganic porous material.

8. A photoreflective sheet of claim 6, wherein one of the metal foil or the base cloth is laminated on said resin foam sheet by fusion-welding.

9. A photoreflective sheet of claim 6, wherein the resin foam sheet is a polyurethane foam sheet.

10. A photoreflective sheet according to claim 6 or 9, wherein the thickness of said resin foam sheet is from about 1 to 5 mm.

11. A photoreflective sheet of claim 6, wherein said porous microcapsule contains at least one sustained release preparation selected from the group consisting of a repellent for animals, a repellent for birds and a repellent for insects, an insecticide, a herbicide and a fungicide.

* * * * *